(12) United States Patent
Barrett et al.

(10) Patent No.: US 11,883,846 B2
(45) Date of Patent: Jan. 30, 2024

(54) METHOD FOR MANUFACTURING AN ULTRASOUND TRANSDUCER AND ULTRASOUND PROBE

(71) Applicant: GE Precision Healthcare LLC, Wauwatosa, WI (US)

(72) Inventors: Jason Barrett, Queen Creek, AZ (US); Flavien Daloz, Antibes (FR); Jessica Abraham, Chandler, AZ (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 1087 days.

(21) Appl. No.: 16/441,254

(22) Filed: Jun. 14, 2019

(65) Prior Publication Data
US 2020/0391245 A1     Dec. 17, 2020

(51) Int. Cl.
| | |
|---|---|
| *B06B 1/06* | (2006.01) |
| *H10N 30/06* | (2023.01) |
| *H10N 30/20* | (2023.01) |
| *H10N 30/088* | (2023.01) |
| *A61B 8/00* | (2006.01) |

(52) U.S. Cl.
CPC ........... *B06B 1/0622* (2013.01); *H10N 30/06* (2023.02); *H10N 30/088* (2023.02); *H10N 30/20* (2023.02); *A61B 8/4483* (2013.01)

(58) Field of Classification Search
CPC ....... B06B 1/0622; H01L 41/09; H01L 41/29; H01L 41/338; A61B 8/4483
See application file for complete search history.

(56) References Cited

U.S. PATENT DOCUMENTS

| | | | |
|---|---|---|---|
| 5,329,496 A * | 7/1994 | Smith | B06B 1/064 |
| | | | 600/459 |
| 5,381,385 A | 1/1995 | Greenstein | |

(Continued)

FOREIGN PATENT DOCUMENTS

| | | | | |
|---|---|---|---|---|
| EP | 0468506 A2 * | 1/1992 | ............... | B06B 1/06 |
| EP | 1318551 A2 * | 6/2003 | ........... | B06B 1/0622 |

(Continued)

OTHER PUBLICATIONS

Richard Goldberg et al., "Performance of Multi-Layer 2-D Transducer Arrays", Proceedings of the IEEE Ultrasonics Symposium, pp. 1103-1106, 1993.

(Continued)

*Primary Examiner* — Jeffrey T Carley

(57) ABSTRACT

A method for making ultrasound transducers and ultrasound probes includes providing a piezoelectric layer having a first surface and a second surface, where the second surface is on an opposite side of the piezoelectric layer from the first surface. The method includes fabricating a plurality of conductive through vias extending from the first surface to the second surface of the piezoelectric layer, where fabricating the plurality of conductive through vias comprises cutting a plurality of trenches through the piezoelectric layer and filling each of the plurality of trenches with a conductive material. The method includes cutting the piezoelectric layer into a plurality of transducer units after fabricating the plurality of conductive through vias and cutting each of the transducer units into a plurality of transducer elements.

20 Claims, 9 Drawing Sheets

(56) References Cited

U.S. PATENT DOCUMENTS

| | | | |
|---|---|---|---|
| 5,704,105 A | 1/1998 | Venkataramani | |
| 5,855,049 A * | 1/1999 | Corbett, III | B06B 1/0622 29/25.35 |
| 5,938,612 A * | 8/1999 | Kline-Schoder | G01S 15/8956 600/459 |
| 6,088,894 A * | 7/2000 | Oakley | B06B 1/064 29/25.35 |
| 6,341,408 B2 * | 1/2002 | Bureau | B06B 1/0622 29/25.35 |
| 6,437,487 B1 | 8/2002 | Mohr, III | |
| 6,483,225 B1 | 11/2002 | Spigelmyer | |
| 7,439,656 B2 * | 10/2008 | Ossmann | G10K 11/02 310/334 |
| 2003/0028108 A1 * | 2/2003 | Miller | A61B 8/4483 600/437 |
| 2003/0073906 A1 * | 4/2003 | Flesch | A61B 8/4494 600/459 |
| 2004/0251784 A1 * | 12/2004 | Kuniyasu | B06B 1/064 257/E27.006 |
| 2006/0067029 A1 * | 3/2006 | Kuniyasu | H01L 41/338 361/302 |
| 2007/0222339 A1 * | 9/2007 | Lukacs | B06B 1/0622 310/334 |
| 2008/0238259 A1 * | 10/2008 | Osawa | H01L 41/293 310/334 |
| 2014/0221840 A1 * | 8/2014 | Ko | A61B 8/4444 600/459 |
| 2016/0033454 A1 * | 2/2016 | Matsuda | H01L 41/08 29/25.35 |
| 2017/0288638 A1 * | 10/2017 | Wildes | H01L 41/277 |
| 2018/0169701 A1 * | 6/2018 | Daloz | B06B 1/0622 |
| 2018/0175278 A1 | 6/2018 | Daloz | |

FOREIGN PATENT DOCUMENTS

| | | | |
|---|---|---|---|
| KR | 20190077289 A | 7/2019 | |
| WO | WO-9421388 A1 * | 9/1994 | A61B 8/4483 |

OTHER PUBLICATIONS

KR patent application 10-2019-0075816 (publication No. KR20190077289) English Abstract obtained from Espacenet.com Oct. 23, 2020, 1 page.

PCT application PCT/US2020/035872 filed Jun. 3, 2020—International Search Report/Written Opinion dated Sep. 11, 2020, 11 pages.

* cited by examiner

METHOD FOR MANUFACTURING AN ULTRASOUND TRANSDUCER AND ULTRASOUND PROBE

BACKGROUND OF THE INVENTION

The subject matter disclosed herein relates generally to a method for manufacturing ultrasound transducers and ultrasound probes.

Ultrasound imaging systems typically include an ultrasound transducer, that performs various ultrasound scans. While some ultrasound transducers only include a single transducer element, most ultrasound transducers used for diagnostic medical imaging include a plurality of individual transducer elements. The transducer elements transmit ultrasound energy and receive ultrasound signals based on the reflected ultrasound energy. The transducer elements may be arranged in an array. The ultrasound signals received by the transducer elements are used to generate an image of one or more anatomical structures within a patient Transducer elements in an ultrasound transducer typically include a piezoelectric material that changes shape in response to the application of a voltage across the piezoelectric material. Changing the potential applied across the piezoelectric material is responsible for generating the ultrasound energy. In order to apply an potential across each of the transducer elements, it is necessary to have two electrical contacts for each of the transducer elements, where the electrical contacts are electrically isolated from each other. The electrical contacts typically include a positive contact and a ground contact for each transducer element.

Ultrasound transducers may include multiple different acoustic layers mounted to a flexible circuit. The layers include a piezoelectric layer, and may include a dematching layer, and/or one or more matching layers. Conventional ultrasound transducers typically employ a "wrap-around" ground comprising a conductive material that electrically connects one of the surfaces of the piezoelectric layer with the flexible circuit. Using a "wrap-around" ground requires performing many of the ultrasound transducer fabrication steps for each individual ultrasound transducer, which leads to a high unit-cost of production for each ultrasound transducer. It would be more cost-effective to perform more of the ultrasound transducer fabrication steps on a wafer-level, as opposed to performing most of the ultrasound transducer fabrication steps on each individual ultrasound transducer.

For at least the reasons discussed above, there exists a need for a novel manufacturing technique for ultrasound transducers and ultrasound probes that allows for the wafer-level manufacturing of ultrasound transducers.

BRIEF DESCRIPTION OF THE INVENTION

In an embodiment, a method for making ultrasound transducers includes providing a piezoelectric layer having a first surface and a second surface, where the second surface is on an opposite side of the piezoelectric layer from the first surface. The method includes fabricating a plurality of conductive through vias extending from the first surface to the second surface of the piezoelectric layer, where fabricating the plurality of conductive through vias comprises cutting a plurality of trenches in the piezoelectric layer and filling each of the plurality of trenches with a conductive material. The method includes cutting the piezoelectric layer into a plurality of transducer units after fabricating the plurality of conductive through vias and cutting each of the transducer units into a plurality of transducer elements.

In an embodiment, a method for making an plurality of ultrasound probes includes providing a piezoelectric layer having a first surface and a second surface, where the second surface is on an opposite side of the piezoelectric layer from the first surface. The method includes fabricating a plurality of conductive through vias extending from the first surface to the second surface of the piezoelectric layer, where fabricating the plurality of conductive through vias includes cutting a plurality of trenches through the piezoelectric layer and filling each of the plurality of trenches with a conductive material. The method includes cutting the piezoelectric layer into a plurality of transducer units after fabricating the plurality of conductive through vias, cutting each of the transducer units into a plurality of transducer elements and securing each one of the plurality of transducer units into a different ultrasound probe body.

DETAILED DESCRIPTION OF THE INVENTION

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Figure 1A:
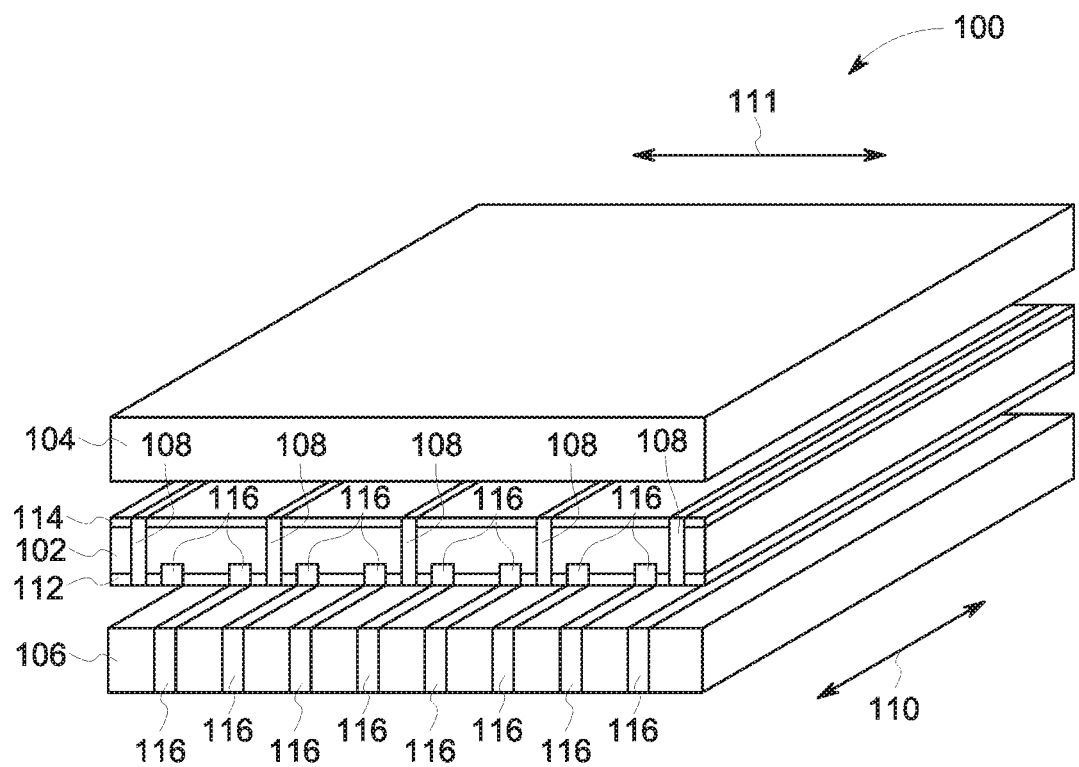
FIG. 1A is a schematic representation of an exploded perspective view of an acoustic stack in accordance with an embodiment.

FIG. 1A is a schematic representation of an exploded perspective view of an acoustic stack 100 in accordance with an embodiment. The acoustic stack 100 includes a piezoelectric layer 102, a matching layer 104, and a dematching layer 106. The piezoelectric layer 102 comprises a piezoelectric material, such as lead zirkonate titanate (PZT), lead titanate (PT), Lead Metaniobate (PbNb2O6), or any other material with piezoelectric properties that may be configured to emit ultrasound energy.

As described above, the piezoelectric layer 102 is made of a material with piezoelectric properties. This means that the piezoelectric layer 102 is made of a material with a structure that mechanically changes shape in response to the application of an electrical potential across the piezoelectric layer 102. Changing the potential applied across the piezoelectric layer 102 at a specific frequency causes the piezoelectric layer 102 to emit ultrasound energy. In order to apply a potential across the piezoelectric layer 102 for each element, it is necessary to have two contact points that are electrically isolated from each other. As a convention, one of these contacts is usually referred to as a positive contact and the other is referred to as a ground contact. However, it should be appreciated that the ground contact may not actually be at electrical ground. Instead, the ground contact just needs to be at a lower potential than the positive contact. Additionally, the positions of the positive contact and the ground contact may be switched, as the polarity of the potential applied across the piezoelectric layer 102 does not matter for purposes of emitting ultrasound energy.

The matching layer 104 is a material with an acoustic impedance between that of the material used for the piezoelectric layer 102 and the patient's tissue. The thickness of the matching layer 104 is typically ¼ of the wavelength of the ultrasound produced by the piezoelectric layer 102, although the matching layer 104 may be different thicknesses according to various embodiments. Matching layers are well-known to those skilled in the art. While the embodiment shown in FIG. 1A has a single matching layer 104, other embodiments may include two or more matching layers in place of the matching layer 104. Embodiments with multiple matching layers may include a second matching layer, attached to an opposite side of the first matching layer from the piezoelectric layer 102, with a second acoustic impedance. The use of multiple matching layers may help to minimize the amount of ultrasound energy reflected back from the patient's tissue due to a mismatch of acoustic impedances between the tissue and an ultrasound probe while imaging.

The dematching layer 106 comprises a material with a higher acoustic impedance than the piezoelectric layer 102. According to many embodiments, it may be desirable to use a material for the dematching layer 106 with an acoustic impedance that is at least two times the acoustic impedance of the piezoelectric layer 102. The piezoelectric layer 102 typically has an acoustic impedance of around 37 MRayls and human tissue typically has an acoustic impedance of around 1.5 MRayls. The dematching layer 106 has an acoustic impedance significantly higher than the acoustic impedance of the piezoelectric layer 102. For example, the dematching layer 106 may have an acoustic impdedance of greater than 40 MRayls, and many embodiment may use a material for the dematching layer 106 with an acoustic impedance of greater than 100 MRayls.

Figure 1B:
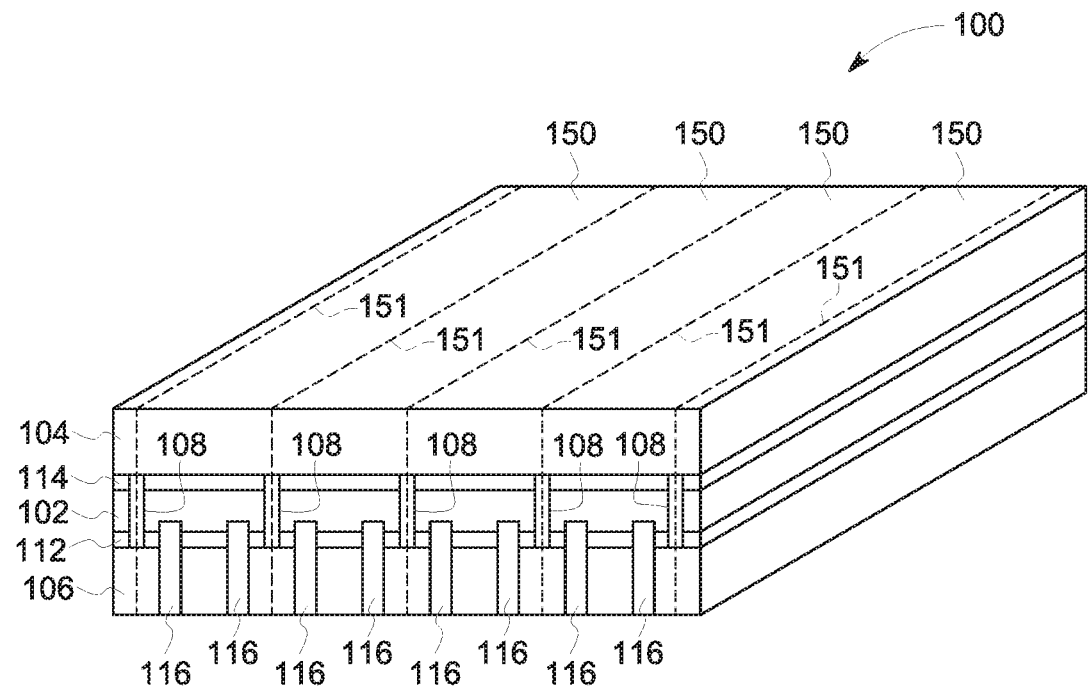
FIG. 1B is a schematic representation of a perspective view of the acoustic stack in accordance with an embodiment.
Figure 1C:
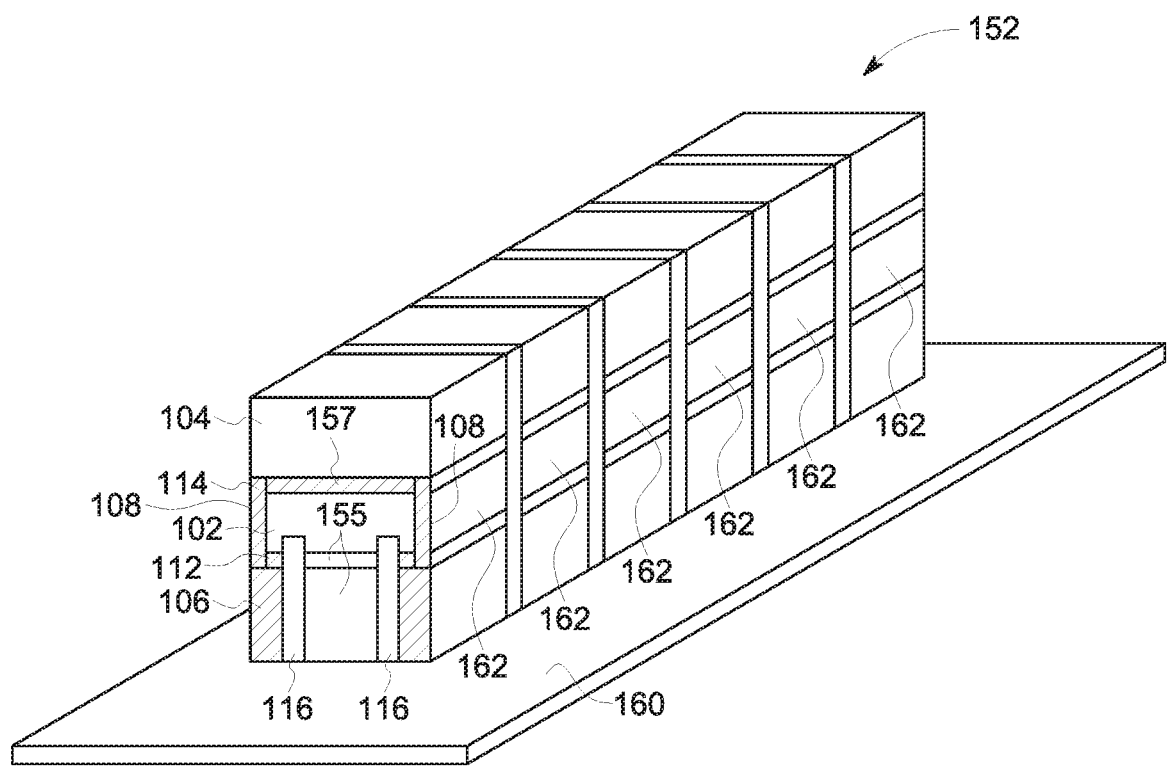
FIG. 1C is a schematic representation of a perspective view of an ultrasound transducer in accordance with an embodiment.

FIG. 1B shows a schematic representation of a perspective view of the acoustic stack 100 in accordance with an embodiment, and FIG. 1C shows a schematic representation of the perspective view of the ultrasound transducer 150 that may be manufactured in accordance with an embodiment. Common reference numbers will be used to identify identical components in FIGS. 1A, 1B, and 1C.

According to the embodiment shown in FIGS. 1A, 1B, and 1C, a first conductive layer 112 is attached to a first surface of the piezoelectric layer 102 and a second conductive layer 114 attached to a second surface of the piezoelectric layer 102, where the second surface is on the opposite side of the piezoelectric layer 102 from the first surface. According to an embodiment, the first conductive layer 112 and the second conductive layer 114 may be attached to the piezoelectric layer 102 after the piezoelectric layer 102 has been cut to the appropriate dimensions for the acoustic stack 100. The first conductive layer 112 and the second conductive layer 114 may be deposited on the piezoelectric layer 102 by sputtering a conductive material, such as gold or copper, on the first surface and the second surface of the piezoelectric layer 102. According to other embodiments, the first conductive layer 112 may be added to the dematching layer 106 and/or the second conductive layer 114 may be added to the matching layer 104 instead of adding both the first conductive layer 112 and the second conductive layer 114 to the piezoelectric layer 102.

According to the first embodiment, as described with respect to FIGS. 1A, 1B, and 1C, a plurality of conductive through vias 108 are fabricated in the piezoelectric layer 102. As shown in FIGS. 1A, 1B, and 1C, the conductive through vias 108 may extend all the way through the first conductive layer 112 and the second conductive layer 114. Each of the conductive through vias 108 extends from a first side of the piezoelectric layer 102 to a second side of the piezoelectric layer 102. In other words, each of the conductive through vias 108 extends all the way through the piezoelectric layer 102. Each of the conductive through vias 108 is fabricated by cutting a plurality of trenches through the piezoelectric layer 102, the first conductive layer 112, and the second conductive layer 114, where each of the plurality of trenches is parallel to an azimuthal direction 110. After forming the plurality of trenches through the piezoelectric layer 102, the first conductive layer 112, and the second conductive layer 114, the trenches are filled with a conductive material, such as an epoxy with a conductive additive. According to other embodiments, the conductive through vias 108 may be fabricated in the piezoelectric layer 102 before the first conductive layer 112 and the second conductive 114 are attached to the piezoelectric layer 102. It should be appreciated that in these embodiments, the conductive through vias may not extend through the first conductive layer 112 and the second conductive layer 114.

According to an embodiment, a plurality of non-conductive vias 116 may be fabricated by cutting a second plurality of trenches through the dematching layer 106 and into the piezoelectric layer 102 either before, after or in parallel with the fabrication of the conductive through vias 108. Each of the non-conductive vias 116 may be fabricated by cutting a trench through the dematching layer 106 and into the piezoelectric layer 102 and filling each of the trenches with a dielectric material, such as an epoxy with a dielectric additive. Each of the second plurality of trenches cut through the dematching layer 106 may align with a trench cut into the piezoelectric layer 102 when the dematching layer 106 is attached to the piezoelectric layer 102. As with the conductive through vias 108, the second plurality of trenches used in the fabrication of the non-conductive vias 116 are cut along the azimuthal direction 110.

After fabricating the conductive through vias 108 and the non-conductive vias 116, the matching layer 104 is attached to the second conductive layer 114 and the dematching layer 106 is attached to the first conductive layer 112 in order to form the acoustic stack 100 shown in FIG. 1B. For purposes of this disclosure, the term "attaching" covers both directly attaching and indirectly attaching. Additionally, the term "attaching" may comprise laminating, bonding via an adhesive, connecting with a mechanical connection, or attaching indirectly via another layer, such as either the first conductive layer 112 or the second conductive layer 114.

Figure 2:
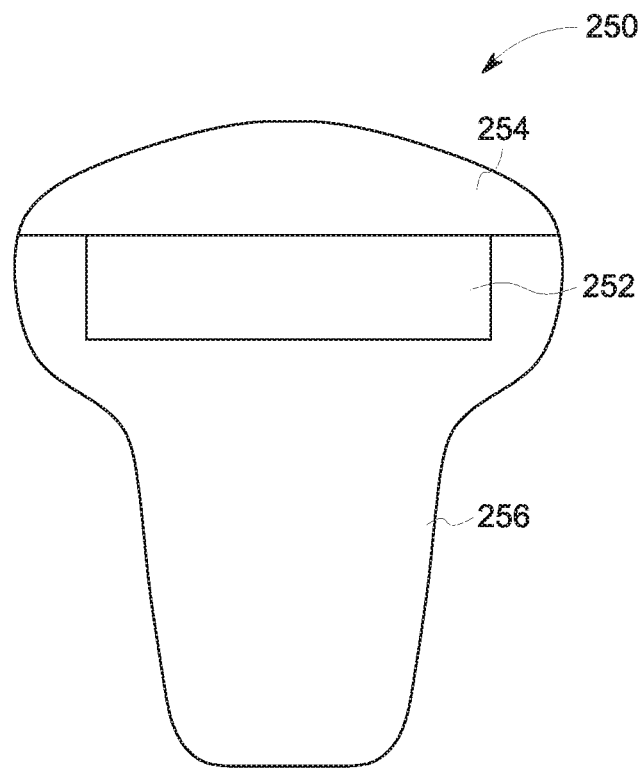
FIG. 2 is a schematic representation of a sectional view of an ultrasound probe according to an embodiment.

Next, the acoustic stack 100 is cut into a plurality of transducer units 150. The acoustic stack 100 shown in FIG. 1B will be cut into 4 separate transducer units 150. According to an embodiment, the acoustic stack 100 is cut along each of the plurality of conductive through vias 108. For example, each cut may be made through the center of a conductive through via 108. The dashed lines 151 shown in FIG. 2 represent the locations of the cuts made to separate the acoustic stack 100 into the plurality of transducer units 150.

Next, each of the transducer units 150 is mounted to an integrated circuit, such as a flexible circuit 160, and the transducer unit 150, including the piezoelectric layer 102, is cut into plurality of individual transducer elements 162 as shown in FIG. 3. While not shown in FIG. 3, the transducer unit 150 may be connected to the integrated circuit 160 with an interposer, or the transducer unit 150 may be mounted to the flexible circuit 160 without an interposer. The embodiment shown in FIG. 3 shows a linear array with 6 individual transducer elements 162. It should be appreciated that FIG. 1A, 1B, and 1C are all schematic representations and that each acoustic stack may of a size to be include more than 4 transducer units and that each transducer unit could be cut to create a different number of elements. For example, linear arrays commonly have significantly more than 6 elements. Linear arrays with any number of elements may be manufactured according to the method described above. FIG. 1C shows an example of an ultrasound transducer 152, after it has been cut from the acoustic stack 100, mounted to the flexible circuit 160, and cut into a plurality of transducer elements 162.

In the embodiment shown in FIG. 1C, cutting the transducer unit 150 into the plurality of transducer elements 162 comprises cutting through the matching layer 104, the second conductive layer 114, the piezoelectric layer 102, the first conductive layer 112 and the dematching layer 106. In order to form individual transducer elements, it is necessary to cut at least most of the way through the piezoelectric layer 102. For example, it is necessary to cut at least 75% of the way through piezoelectric layer 102 in order to differentiate the transducer elements 162. After separating the transducer elements 162, the cuts may be filled with a filler, such as an epoxy, or an epoxy with an additive, or the cuts may be left unfilled. Therefore, according to other embodiments, cutting the transducer elements 162 may include cutting through the matching layer 104 and into some or all of the piezoelectric layer 102 without cutting into the dematching layer 106. After mounting the transducer unit 150 to the flexible circuit 160 and cutting the transducer unit 150 into individual transducer elements 162, the ultrasound transducer 152 may be installed in a probe body to form an ultrasound probe.

In FIG. 1C, the two non-conductive vias 116 allow for the application of an electrical potential across the piezoelectric layer 102. For example, a first portion 155 may be at a first potential while a second portion 157, indicated with hatching, may be at a second electric potential, that is different than the first potential. According to convention, the first region 155 may be considered to be at a positive potential, while the second region 157 may be considered to be at electrical ground. However, in practice, the potentials may be reversed (i.e., the first region 155 may be at electrical ground and the second region 157 may be at a positive potential). Additionally, neither the first region 155 nor the second region 157 may be at true electrical ground. In order to make the piezoelectric layer 102 vibrate, it is necessary to apply a potential difference across the piezoelectric layer 102.

The conductive through vias 108 enable electrical connections between the flexible circuit 160 and the portion of the piezoelectric layer 102 in contact with the second region 157. The non-conductive vias 116 provide the electrical separation needed to apply an electrical potential across the piezoelectric layer 102. The conductive through vias 108 in combination with the non-conductive vias 116 enable the piezoelectric layer 102 to have the necessary electrical connections with the flexible circuit 160 even when manufactured at a wafer-level. For purposes of this disclosure, the term "wafer-level" will be defined to include manufacturing methods or processes performed on an acoustic stack that is eventually subdivided to form two or more individual ultrasound transducers. The embodiment described with respect to FIGS. 1A, 1B, and 1C allows for wafer-level manufacturing of linear ultrasound transducers.

FIG. 2 is a schematic representation of a sectional view of an ultrasound probe 250 according to an embodiment. The ultrasound probe 250 includes an ultrasound transducer 252, a lens 254 and a probe body 256. The probe body 256 may be a plastic or a composite material. The probe body 256 is adapted to retain the ultrasound transducer 252 and the lens 254. The lens 254 is adapted to focus an acoustic beam emitted from the transducer elements of the ultrasound transducer 252. According to an embodiment, the probe 250 may include the ultrasound transducer 152 in place of the transducer 252.

A second embodiment will be described using FIGS. 1A, 1B, and 1C, even though the process depicted by FIGS. 1A, 1B, and 1C is not exactly the same as the second embodiment. According to the second embodiment, the method may include attaching the dematching layer 106 to the first conductive layer 112 (which is attached to the piezoelectric layer 102) before fabricating either the conductive through vias 108 or the non-conductive vias 116. Once the dematching layer 106 has been attached to the first conductive layer 112 and, indirectly, to the piezoelectric layer 102, the method includes fabricating the conductive through vias 108 by cutting a plurality of trenches through the second conductive layer 114, the piezoelectric layer 102 and through the first conductive layer 112, and then filling the trenches with a conductive material. Fabricating the non-conductive vias 116 may comprise cutting a second plurality of trenches through the dematching layer 106, through the first conductive layer 112 and into the piezoelectric layer 102. Since the dematching layer 106 has already been laminated to the first conductive layer 112 prior to fabricating the second plurality of trenches, it is possible to cut through the dematching layer 106, through the first conductive layer 112 and into the piezoelectric layer 102 with a single cut per trench. Next, the second plurality of trenches are filled with a dielectric material to form the plurality of non-conductive vias 116.

After fabricating the conductive through vias 108 and the non-conductive vias 116, one or more matching layers, such as matching layer matching layer 104, may be attached to the second conductive layer 114 to complete the acoustic stack 100. Next, the acoustic stack 100 is cut into a plurality of transducer units 150, each of which is further machined to create individual transducer elements 162 and attached to an integrated circuit, such as the flex circuit 160, in the same manner that was described with respect to the first embodiment.

Figure 3A:
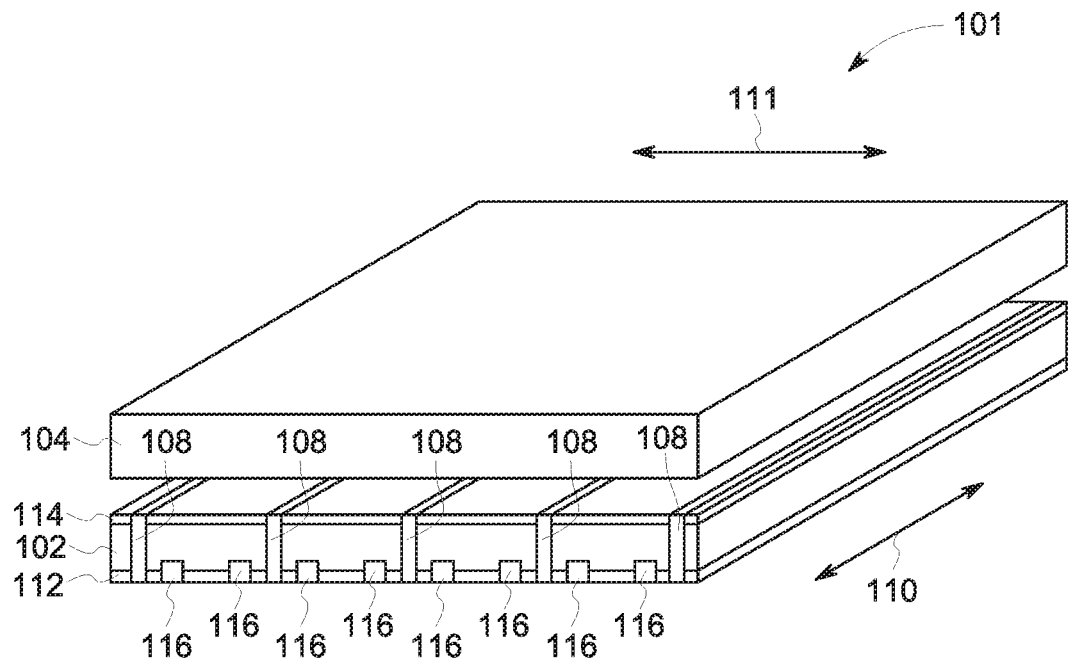
FIG. 3A is a schematic representation of an exploded perspective view of an acoustic stack in accordance with an embodiment.
Figure 3B:
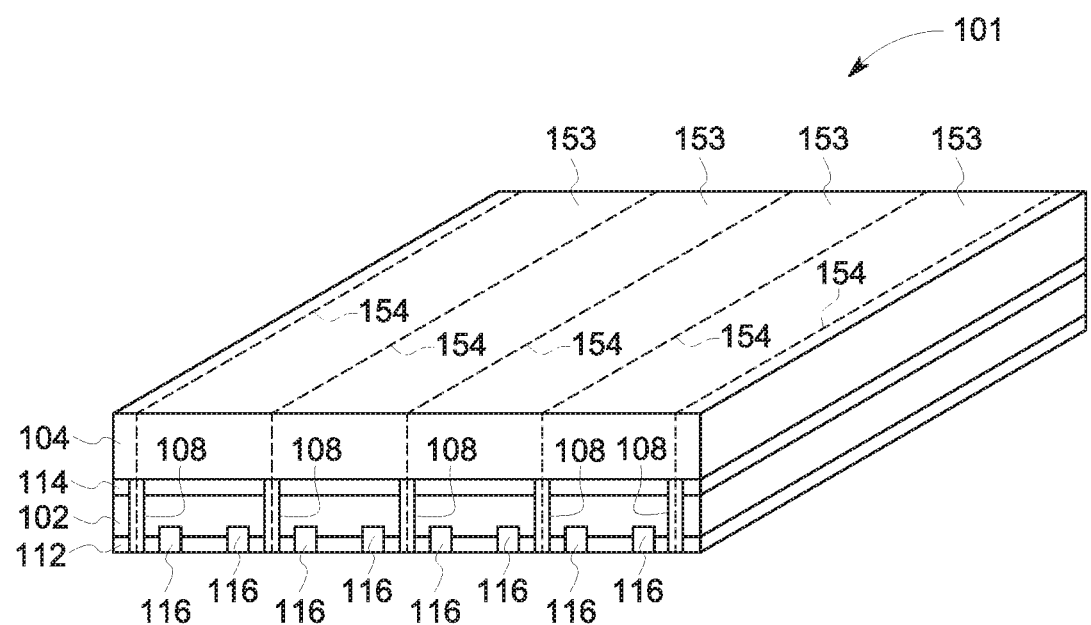
FIG. 3B is a schematic representation of a perspective view of an acoustic stack according to an embodiment.
Figure 3C:
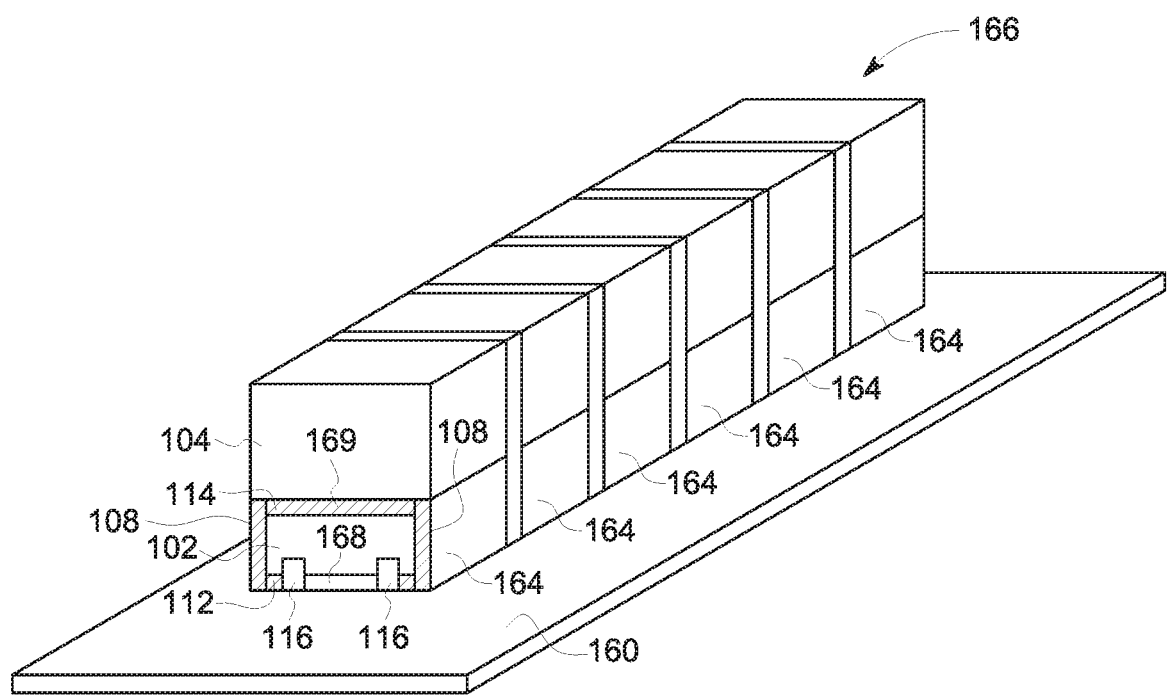
FIG. 3C is a schematic representation of a perspective view of an ultrasound transducer in accordance with an embodiment.

FIG. 3A is a schematic representation of an exploded perspective view of an acoustic stack 101 in accordance with an embodiment. FIG. 3B is a schematic representation of a perspective view of the acoustic stack 101 according to an embodiment, and FIG. 3C is a schematic representation of a perspective view of an ultrasound transducer 166 in accordance with an embodiment. FIGS. 3A, 3B, and 3C will be used to describe a third embodiment for making an ultrasound transducer. Common reference numbers will be used to identify previously described elements.

According to a third embodiment for making an ultrasound transducer, the method includes fabricating a plurality of conductive through vias 108 through the piezoelectric layer 102. The third embodiment will be described with respect to FIGS. 3A, 3B, and 3C. The first conductive layer 112 and the second conductive layer 114 may be attached to the piezoelectric layer 102 before the fabrication of the conductive through vias 108. As described with respect to the previous embodiments, fabricating the conductive through vias 108 may include cutting a first plurality of trenches through the piezoelectric layer 102 and both the first conductive layer 112 and the second conductive layer 114. According to other embodiments, where the first and second conductive layers have not been attached to the piezoelectric layer 102, cutting the first plurality of trenches may include cutting through the piezoelectric layer 102 (and not through either of the conductive layers). After the first plurality of trenches have been cut, the first plurality of trenches are filled with a conductive material, such as epoxy with one or more conductive additives.

Next, the plurality of non-conductive vias 116 are fabricated. As shown in FIGS. 3A, 3B, and 3C, the non-conductive vias 116 may only extend part way into the piezoelectric layer 102. The non-conductive vias 116 electrically separate the first conductive layer 112. Fabricating the non-conductive vias 116 includes cutting a second plurality of trenches through the first conductive layer 112 and into the piezoelectric layer 102. The second plurality of trenches extend in the azimuthal direction 110.

According to other embodiments, the plurality of non-conductive vias 116 may be fabricated before the plurality of conductive through vias 108, or, according to other embodiments, the plurality of non-conductive vias 116 may be fabricated at the same time as the plurality of conductive through vias 108.

Next, the matching layer 104 is attached to the second conductive layer 114 to form acoustic stack 101. After attaching the matching layer 104 to the second conductive layer 114, the acoustic stack 101 is cut into a plurality of individual transducer units 153. According to an embodiment, the acoustic stack 101 may be separated into the individual transducer units 153 by cutting along each of the conductive through vias 108. The dashed lines 154 in FIG. 3B indicate the locations of the cuts that may be used to separate the acoustic stack 101 into the transducer units 153.

After separating the ultrasound units 153, each ultrasound unit 153 is attached to a separate integrated circuit, such as the flexible circuit 160, and then each ultrasound unit 153 is separated into individual transducer elements 164 to form an ultrasound transducer 166 as shown in FIG. 3C. The transducer unit 154 shown in FIG. 3C has been cut to form individual transducer elements 164.

According to an embodiment, cutting the transducer unit 153 into the plurality of transducer elements 164 comprises cutting through the matching layer 104, the second conductive layer 114, the piezoelectric layer 102, and the first conductive layer 112. In order to form individual transducer elements 164, it is necessary to cut at least most of the way through the piezoelectric layer 102. For example, it is necessary to cut at least 75% of the way through the piezoelectric layer 102 in order to differentiate the transducer elements 164. After separating the transducer elements 164, the cuts may be filled with a filler, such as an epoxy, or an epoxy with an additive, or the cuts may be left unfilled. After mounting the transducer unit 153 to the flexible circuit 160 and cutting the transducer unit 153 into the individual transducer elements 164, each ultrasound transducer 166 may be installed in a probe body to form an ultrasound probe. For example, according to an embodiment, the ultrasound transducer 166 may be attached to a probe body such as the probe body 256 in place of the ultrasound transducer 252.

In FIG. 3C, the two non-conductive vias 116 allow for the application of an electrical potential across the piezoelectric layer 102. For example, a first region 168 may be at a first potential while a second region 169, indicated with hatching, may be at a second electric potential, that is different than the first potential. According to convention, the first region 168 may be considered to be at a positive potential, while the second region 169 may be considered to be at electrical ground. However, in practice, the potentials may be reversed (i.e., the first region 168 may be at electrical ground and the second region 169 may be at a positive potential). Additionally, neither the first region 168 nor the second region 169 may be at true electrical ground. In order to make the piezoelectric layer 102 vibrate, it is only necessary to apply a potential difference across the piezoelectric layer 102. The conductive through vias 108 enable electrical connections between the flexible circuit 160 and the portion of the piezoelectric layer 102 in contact with the second region 169.

Figure 4A:
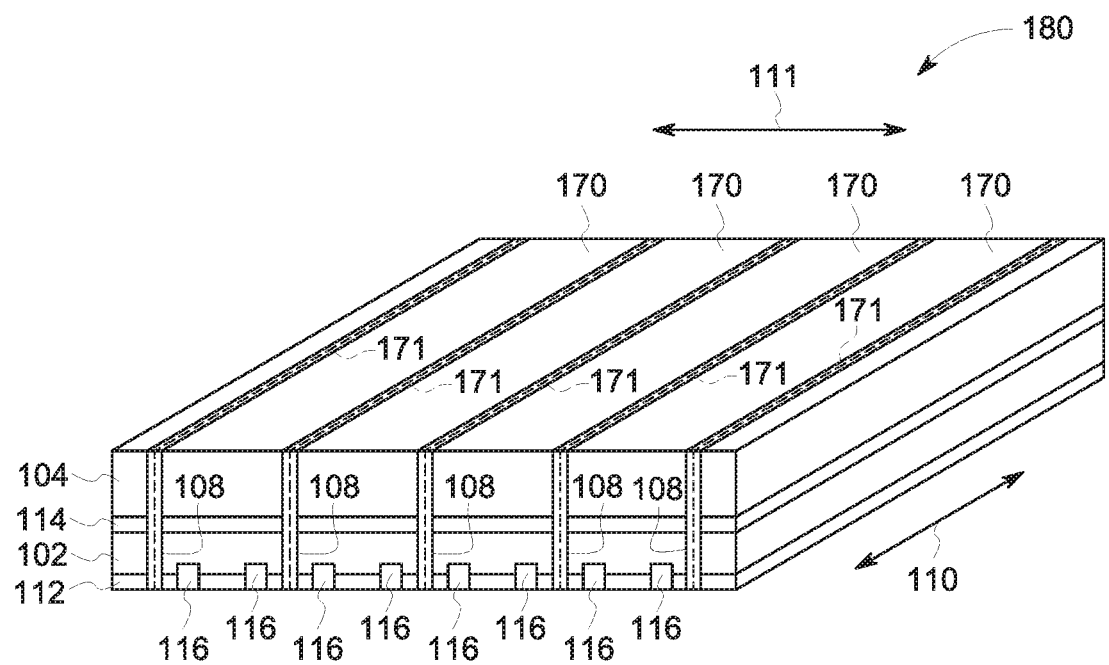
FIG. 4A is a schematic representation of a perspective view of an acoustic stack in accordance with an embodiment.
Figure 4B:
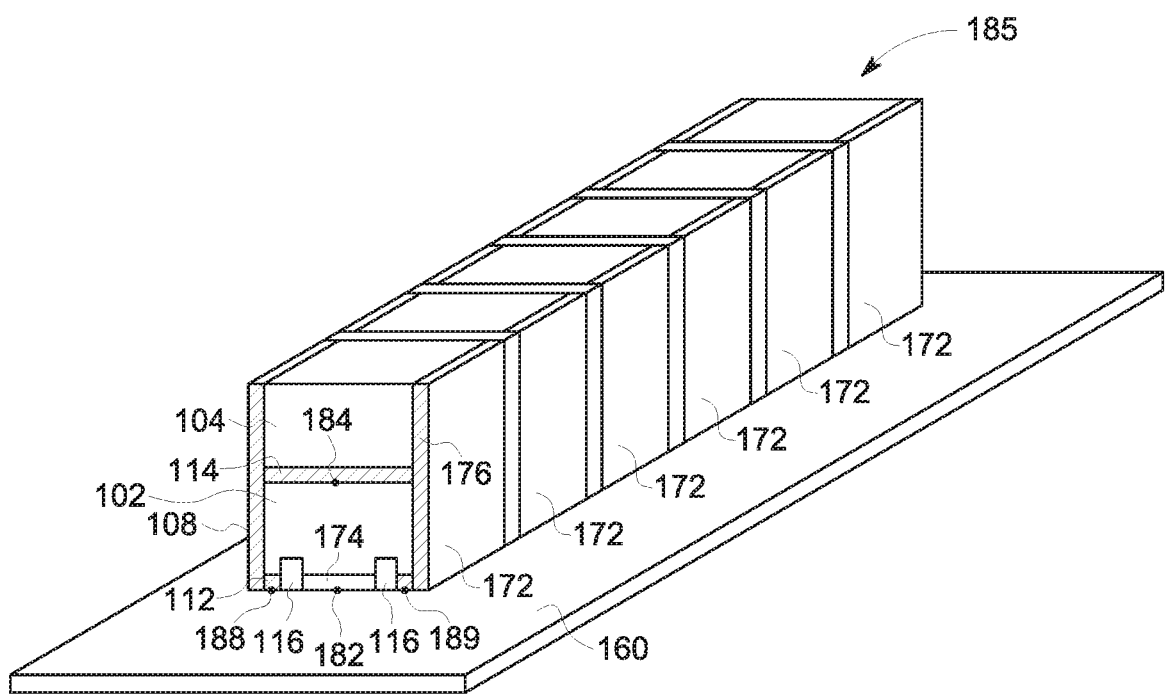
FIG. 4B is schematic representation of a perspective view of an ultrasound transducer in accordance with an embodiment.

FIG. 4A is a schematic representation of a perspective view of an acoustic stack 180 in accordance with an embodiment and FIG. 4B is schematic representation of a perspective view of an ultrasound transducer 185 in accordance with an embodiment. Both FIGS. 4A and 4B will be described with respect to a fourth embodiment. Common reference numbers will be used to identify previously described elements.

As discussed previously, the first conductive layer 112 and the second conductive layer 114 may be attached to the piezoelectric layer 102 through a process such as lamination or sputtering. According to the fourth embodiment, a method of manufacturing an ultrasound transducer may include first attaching the matching layer matching layer 104 to the second conductive layer 114 (which is attached to the piezoelectric layer 102). In other embodiments, the matching layer 104 may be replaced with two or more matching layers, each with a different acoustic impedance that are laminated to the piezoelectric layer 102. After attaching the matching layer 104 to the second conductive layer 114 (and indirectly attaching the matching layer 104 to the piezoelectric layer 102), the method includes fabricating the plurality of conductive through vias 108 and the plurality of non-conductive vias 116.

According to the fourth embodiment, fabricating the conductive through vias 108 may comprise cutting a first plurality of trenches in the azimuthal direction 110 and then filling the first plurality of trenches with a conductive material, such as an epoxy with one or more conductive additives. As shown in FIG. 4A, the conductive through vias 108 extend through the matching layer 104, the second conductive layer 114, the piezoelectric layer 102 and the first conductive layer 112. Therefore, cutting the first plurality of trenches comprises cutting the first plurality of trenches through the matching layer 104, the second conductive layer 114, the piezoelectric layer 102, and the first conductive layer 112. Since the matching layer 104 is attached to the second conductive layer 114 prior to cutting the trenches, it is possible to fabricate each of the trenches with a single cut through the matching layer 104, the second conductive layer 114, the piezoelectric layer 102 and the first conductive layer 112.

The plurality of non-conductive vias 116 are fabricated by cutting a second plurality of trenches through the first conductive layer 116 and into the piezoelectric layer 102. The second plurality of trenches are also in the azimuthal direction 110. The second plurality of trenches are then filled with a dielectric material in order to form the plurality of non-conductive vias 116. Each of the non-conductive vias 116 extends all the way through the first conductive layer 112 and into the piezoelectric layer 102.

Next, the acoustic stack 180 is separated into a plurality of individual transducer units 170 by cutting along dashed lines 171, shown in FIG. 4A. According to an embodiment, the cuts may be made along the conductive through vias 108.

Next, each of the transducer units 170 is attached to an integrated circuit, such as the flexible circuit 160. After attaching the transducer unit 170 to the flexible circuit 160, the transducer unit 170 is cut to form a plurality of individual transducer elements 172. The cuts may be filled with a filler, such as epoxy, or the cuts may be left unfilled. According to other embodiments, each transducer unit 170 may be cut to form the individual transducer elements 172 before attaching each transducer unit 170 to the flexible circuit 160. The ultrasound transducer 185 shown in FIG. 4B is a linear array with 6 elements, but it should be appreciated that the same method may be used to fabricate linear arrays with a different number of elements. According to an embodiment, the ultrasound transducer 185 may be attached to a probe body such as the probe body 256 in place of the ultrasound transducer 252.

Referrring to FIG. 4B, according to an embodiment, a positive contact from the flexible circuit 160 may connect to the portion of the first conductive layer 112 indicated by point 182. The opposite side of the piezoelectric layer 102, such as that indicated by point 184 is electrically connected to a ground contact in the flex 160. The ground contact in the flex 160 may be connected to the second conductive layer 114 through an electrical connection in an interposer (not shown). Likewise, an interposer may be used to connect to portions of the first conductive layer 112 indicated by points 188 and 189. Points 188, 189, and 184 are all electically connected by portions of the conductive through via 108 attached to each transducer unit 170. Separating the transducer units 170 by cutting along the conductive through vias 108 provides electrical connections between the first conductive layer 112 and the second conductive layer 114 that is used for either the ground contact (as described hereinabove) or a positive contact according to an embodiment (not shown) with reversed polarity. The non-conductive vias 116 serve to electrically isolate the portion of the first conductive layer at a positive potential, such as point 182, from the portions of the first conductive layer 112 at ground, such as points 188 and 189. The portion of FIG. 4B shown with hatching, indicated by 176, may all be maintained at the same electrical potential. The non-conductive vias 116 shown in FIG. 4B serve to electrically isolate a first side of the piezoelectric layer 102, connected to 174, from the perimeter of the piezoelectric layer 102 that is connected to the hatched portion 176.

Figure 5A:
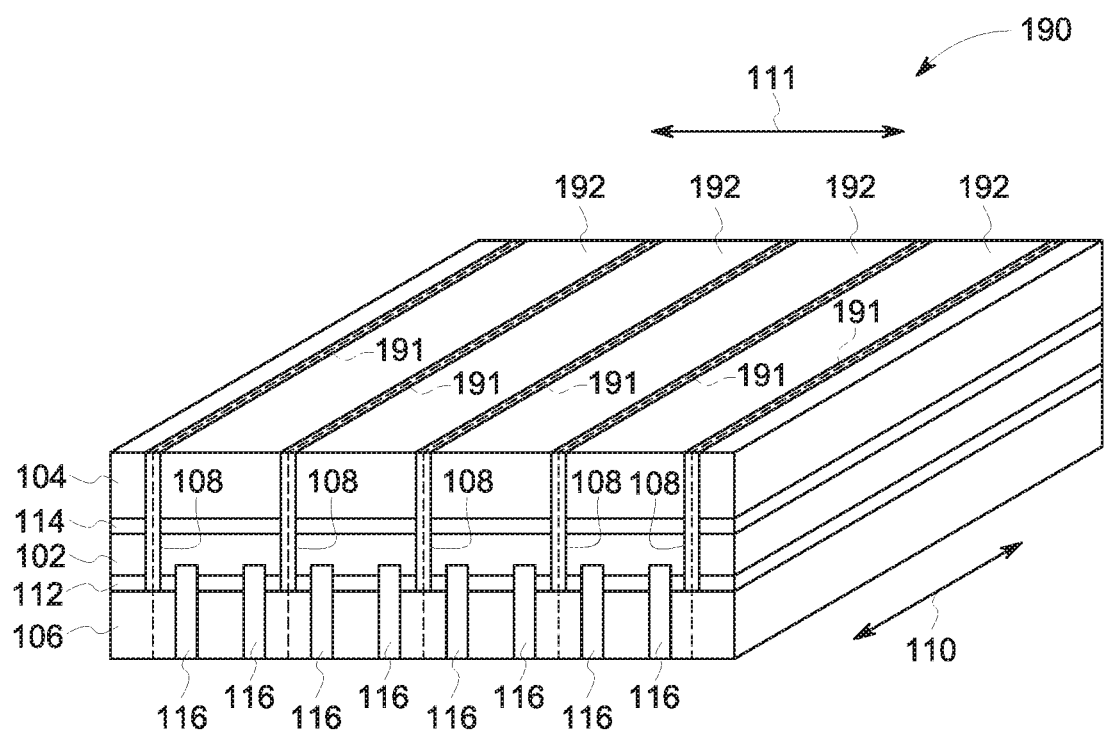
FIG. 5A is a schematic representation of a perspective view of an acoustic stack in accordance with an embodiment.
Figure 5B:
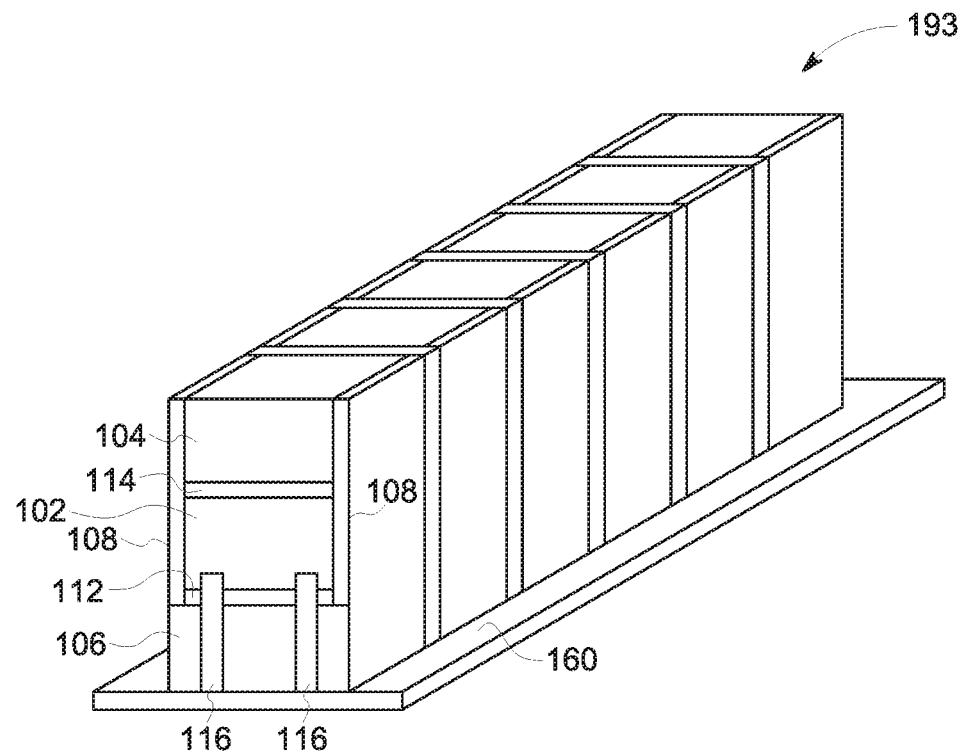
FIG. 5B is a schematic representation of a perspective view of a ultrasound transducer according to an embodiment.

According to a fifth embodiment, the matching layer 104 may be attached to the second conductive layer 114 and the dematching layer 106 may be attached to the first conductive layer 112 before the fabrication of either the conductive through vias 108 or the non-conductive vias 116. After attaching the matching layer 104 and the dematching layer 106, the method includes fabricating the plurality of conductive through vias 108 and fabricating the plurality of non-conductive vias 116. FIG. 5A is a schematic representation of a perspective view of an acoustic stack 190 according to the fifth embodiment. FIG. 5B is a schematic representation of a perspective view of an ultrasound transducer 193 according to the fifth embodiment. FIGS. 5A and 5B will be referenced during the description of the fifth embodiment.

Fabricating the plurality of conductive through vias 108 comprises cutting a first plurality of trenches through the matching layer 104, the second conductive layer 114, the piezoelectric layer 102, and the first conductive layer 112; and then filling the first plurality of trenches with a conductive material. Fabricating the plurality of non-conductive vias 116 comprises cutting a second plurality of trenches through both the dematching layer 106 and the first conductive layer 112 and into the piezoelectric layer 102; and then filling the second plurality of trenches with a dielectric material. According to another embodiment, the method may include fabricating the plurality of non-conductive vias 116 before fabricating the plurality of conductive through vias 108, or embodiments may comprise fabricating the plurality of non-conductive vias 116 and the plurality of conductive through vias 108 in parallel. The acoustic stack 190 may be cut along the dashed lines 191 in order to segment the acoustic stack 190 into a plurality of transducer units 192.

The first five embodiments are applicable for the manufacturing of linear ultrasound transducer arrays. Each transducer element relies on the connection provided by the conductive through vias 108 in order to provide a ground return path from the second conductive layer 114 back to the flexible circuit 160. (Or to provide a positive electrical connection between the flexible circuit 160 and the second conductive layer 114 for embodiments with reversed polarity.) Since the array is only one element wide in an elevation direction 111 in a linear array, the first conductive layer 112 is electrically connected to the second conductive layer 114 for each transducer element even after cutting (dicing) the transducer unit into individual transducer elements. However, this same architecture will obviously not work for transducer designs with more than one element in the elevation direction 111 since cutting the transducer unit into individual transducer elements in the elevation direction would disrupt the electrical connection between the first conductive layer 112 and the second conductive layer 114 provided by the conductive through vias 108. In other words, the conductive through vias 108 would only be able to provide electrical connections for the outer elements; elements that are internal elements (i.e., transducer elements that are surrounded on both the azimuthal and elevation directions by other transducer elements) in a 2D array, for example, would not have the required electrical connection for a ground return. The next two embodiments that will be described will be particularly well-suited for arrays with more than one row of elements in the elevation direction, such as a 1.25D array, a 1.5D array, a 1.75D array, and a 2D matrix array. According to an embodiment, the ultrasound transducer 193 may be attached to a probe body such as the probe body 256 in place of the ultrasound transducer 252.

Figure 6A:
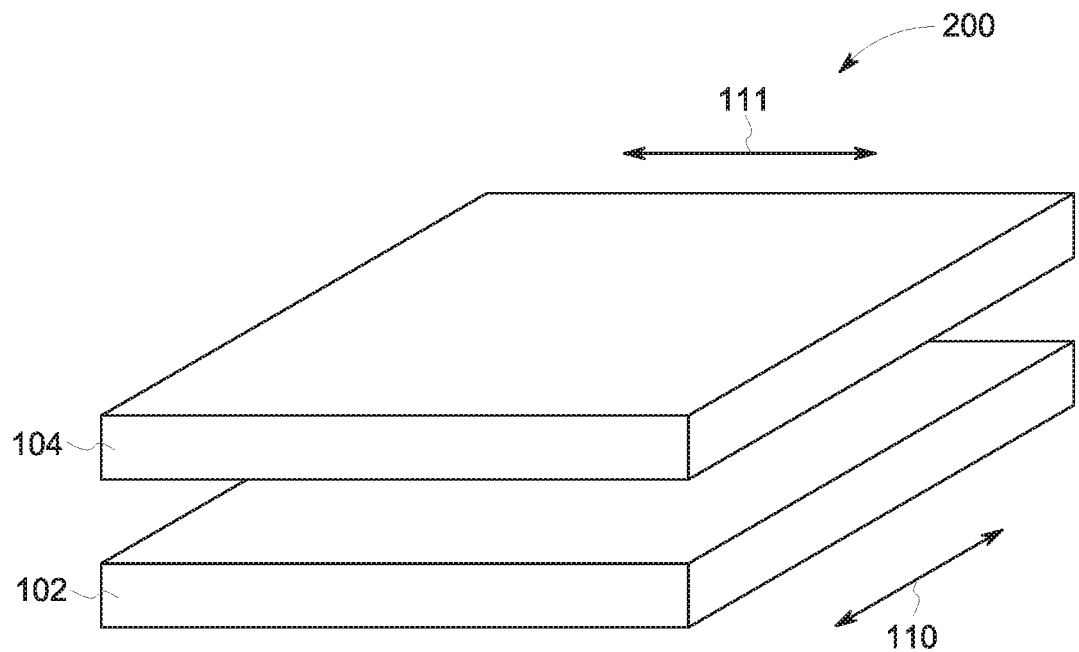
FIG. 6A is a schematic representation of an exploded perspective view of an acoustic stack in accordance with an embodiment.
Figure 6B:
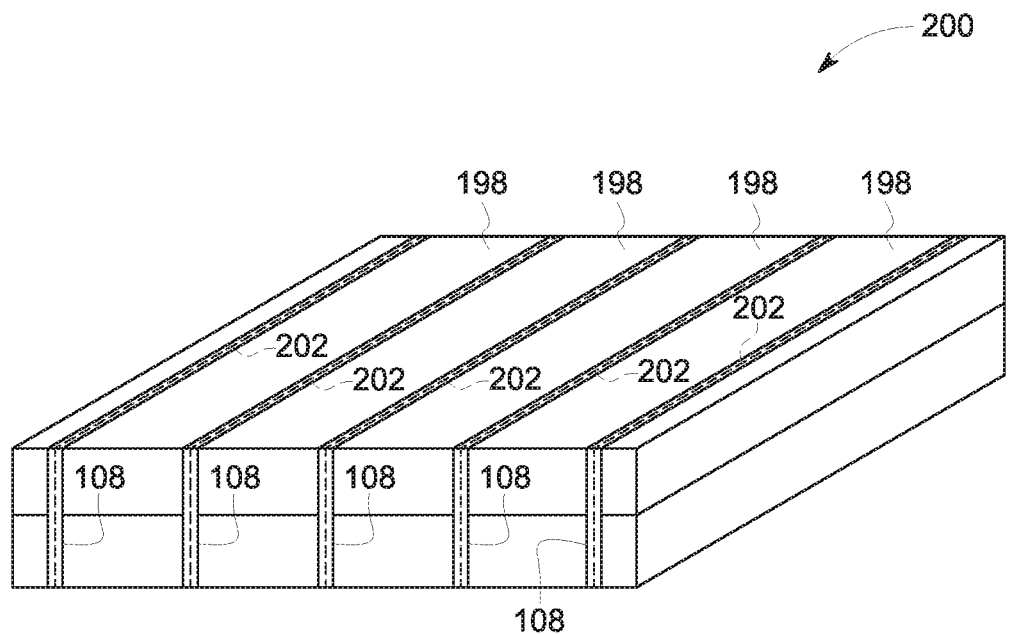
FIG. 6B is a schematic representation of a perspective view of a transducer unit according to an embodiment.
Figure 6C:
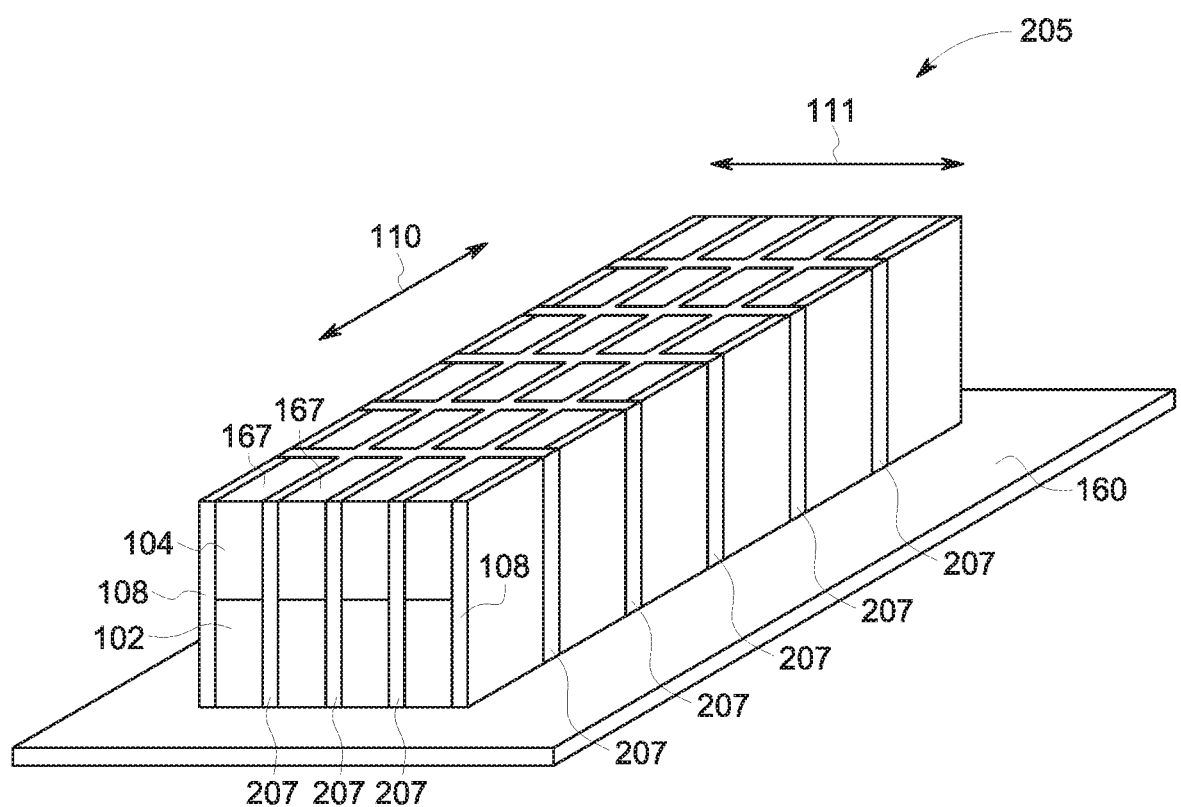
FIG. 6C is a schematic representation of a perspective view of an ultrasound transducer according to an embodiment.

FIGS. 6A is a schematic representation of an exploded perspective view of a acoustic stack 200 in accordance with an embodiment. FIG. 6B is a schematic representation of perspective view of the acoustic stack 200 according to an exemplary embodiment. FIG. 6C is a schematic representation of perspective view of an ultrasound transducer 205 in accordance with an exemplary embodiment. FIGS. 6A, 6B, and 6C will be used to describe a sixth embodiment. Common reference numbers will be used to identify previously described elements.

According to the sixth embodiment, the piezoelectric layer 102 may be attached to the matching layer 104. The plurality of conductive through vias 108 may be fabricated by cutting a first plurality of trenches through the piezoelectric layer 102 and matching layer 104 and then filling the first plurality of trenches with a conductive material, such as an epoxy containing one or more conductive additives. The first plurality of trenches are cut parallel to the azimuthal direction 110.

Next, the acoustic stack 200 is cut into a plurality of separate transducer units 198 by cutting the acoustic stack 200 along each of the dashed lines 202 shown in FIG. 6B. As indicated by the dashed lines 202, the cuts separating the transducer units 198 are positioned along the conductive through vias 108. This cutting process leaves some of the conductive material from the conductive through via 108 on each of the transducer units 198.

FIG. 6C is a schematic representation of a perspective view of an ultrasound transducer 205 in accordance with an embodiment. After fabricating the individual transducer units 198, each transducer unit 198 is attached to an integrated circuit, such as the flexible circuit 160 and a plurality of cuts are made through the matching layer 104 and the piezoelectric layer 102 in order to form individual transducer elements 167. According to an embodiment, each transducer unit 198 may be segmented by cutting in both the azimuthal direction 110 and the elevation direction 111 to generate an array with more than one row of transducer elements in the elevation direction 111. The cuts are filled with a nonconductive material in order to form isolation cuts 207. The isolation cuts 207 acoustically and electrically separate the individual transducer elements 167. While not shown in FIG. 6C, a conductive layer may be placed on top (i.e. on the side opposite of the flexible circuit 160) in order to electrically connect each of the transducer elements 167 with the conductive through vias 108. This may, for instance, be used to provide a ground return connection to each of the transducer elements 167. The conductive through vias 108 provide an electrical return path between each of the transducer elements 167 and the flexible circuit 160. According to an embodiment, a positive electrical contact may be provided between the flexible circuit 160 and each of the transducer elements 167. The isolation cuts 207 may be used to fabricate a 1.25D array, a 1.5D array, a 1.75D array or a 2D matrix array. According to an embodiment, the ultrasound transducer 205 may be attached to a probe body such as the probe body 256 in place of the ultrasound transducer 252.

Figure 7A:
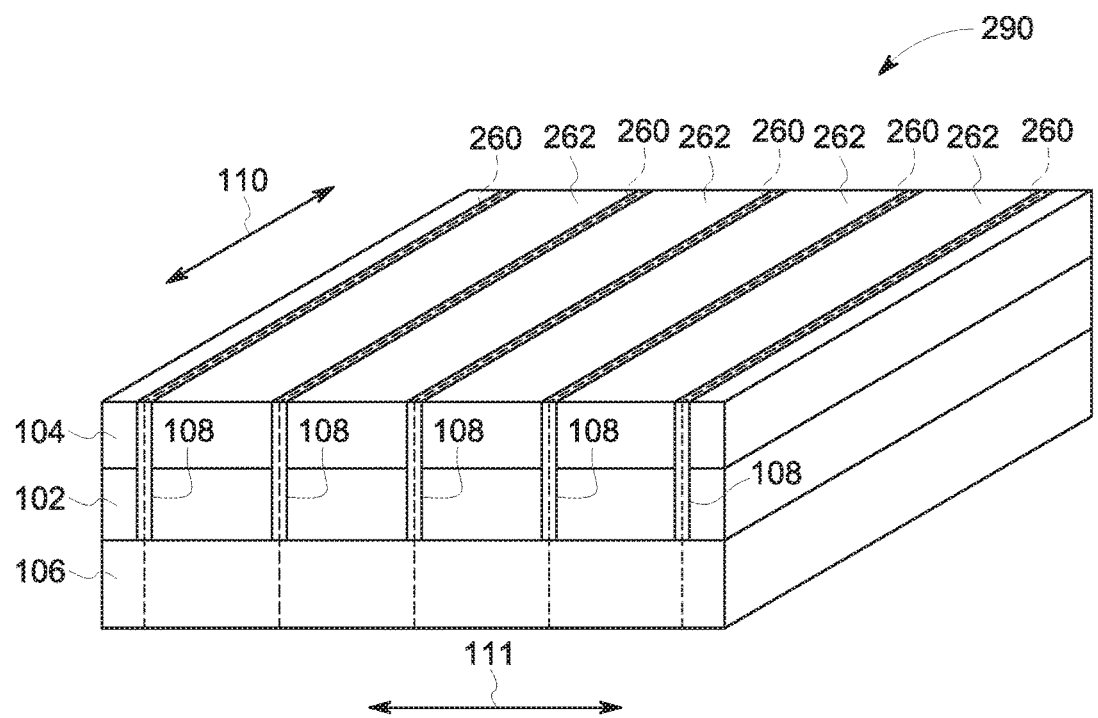
FIG. 7A is a schematic representation of a perspective view of an acoustic stack in accordance with an embodiment.
Figure 7B:
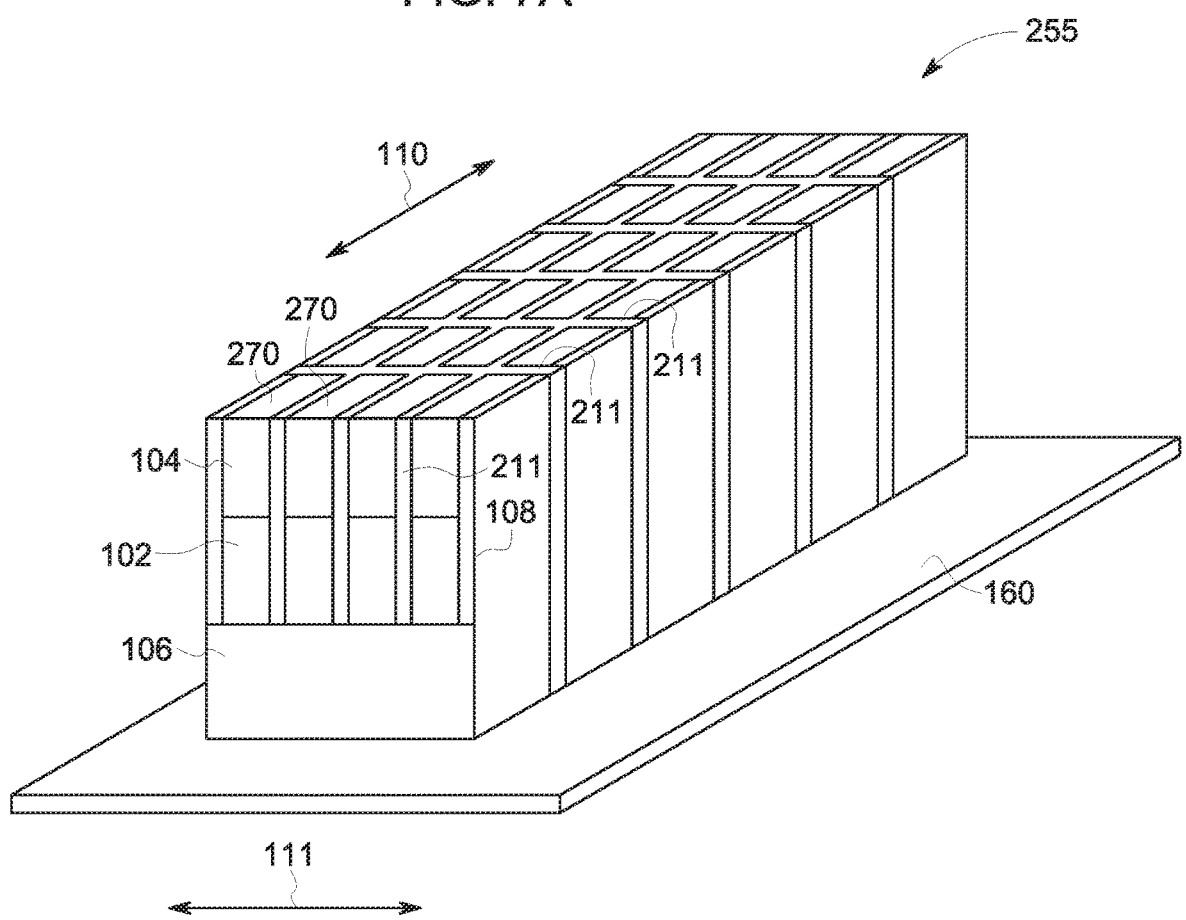
FIG. 7B is a schematic representation of a perspective view of an ultrasound transducer in accordance with an embodiment.

FIG. 7A is schematic representation of a perspective view of an acoustic stack 290 in accordance with an embodiment. FIG. 7B is a schematic representation of a perspective view of an ultrasound transducer 255 in accordance with an embodiment. Common elements are identified with identical reference numbers.

According to an exemplary method of manufacturing ultrasound transducers, the matching layer 104 is attached to the piezoelectric layer 102 and the dematching layer 106 is attached to the piezoelectric layer 102. After attaching the matching layer 104 and the dematching layer 106 to the piezoelectric layer 102, the conductive through vias 108 are fabricated by cutting a plurality of trenches through the matching layer 104 and the piezoelectric layer 102 and filling the plurality of trenches with a conductive material such as conductive epoxy.

Next, the acoustic stack 290 is segmented into a plurality of transducer units 262 by cutting along the dashed lines 260 shown in FIG. 7A. After segmenting the transducer units 262, each transducer unit 262 is attached to an integrated circuit, such as the flexible circuit 160 and then the transducer unit 262 is diced to form a plurality of individual transducer elements 270. Dicing (cutting) may include cutting through the matching layer 104, the piezoelectric layer 102, and the dematching layer 106 according to an embodiment to form a plurality of transducer elements 270. This technique may be appropriate for any type of ultrasound transducer with more than 1 row of elements in the elevation direction, such as a 1.25D array, a 1.5D array, a 1.75D array or a 2D matrix array. As described with respect to FIGS. 6A, 6B, and 6C, each transducer element 270 may be segmented by cutting in both the azimuthal direction 110 and the elevation direction 111 to generate an array with more than one row of transducer elements in the elevation direction 111. The cuts are filled with a nonconductive material in order to form isolation cuts 211. The isolation cuts 211 acoustically and electrically separate the individual transducer elements 270. While not shown in FIG. 6C, a conductive layer may be placed on top (i.e. on the side opposite of the flexible circuit 160) in order to electrically connect each of the transducer elements 270 with the conductive through vias 108. This may, for instance, be used to provide a ground return connection to each of the transducer elements 270. The conductive through vias 108 provide an electrical return path between each of the transducer elements 270 and the flexible circuit 160. According to an embodiment, a positive electrical contact may be provided between the flexible circuit 160 and each of the transducer elements 270. The method may be used to fabricate a 1.25D array, a 1.5D array, a 1.75D array or a 2D matrix array. According to an embodiment, the cuts used to segment the transducer elements 270 may be filled with a material such as an epoxy. According to an embodiment, the ultrasound transducer 255 may be attached to a probe body such as the probe body 256 in place of the ultrasound transducer 252.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for making ultrasound transducers comprising:
    providing a piezoelectric layer having a first surface and a second surface, where the second surface is on an opposite side of the piezoelectric layer from the first surface;
    attaching a first conductive layer to the first surface of the piezoelectric layer;
    attaching a second conductive layer to the second surface of the piezoelectric layer;
    fabricating a plurality of conductive through vias extending from the first surface to the second surface of the piezoelectric layer, where fabricating the plurality of conductive through vias comprises cutting a plurality of trenches through the piezoelectric layer and entirely filling each of the plurality of trenches with an electrically conductive material;
    cutting the piezoelectric layer into a plurality of transducer units after fabricating the plurality of conductive through vias, the plurality of transducer units comprising a first transducer unit and a second transducer unit, wherein said cutting the piezoelectric layer into the plurality of transducer units comprises cutting along one of the plurality of conductive through vias to separate the first transducer unit from the second transducer unit, wherein said cutting along the one of the plurality of conductive through vias leaves a first portion of the conductive material from the one of the plurality of conductive through vias on the first transducer unit and a second portion of the conductive material from the one of the plurality of conductive through vias on the second transducer unit, wherein the first portion of the conductive material provides a first electrical connection between the first conductive layer and the second conductive layer for the first transducer unit and the second portion of the conductive material provides a second electrical connection between the first conductive layer and the second conductive layer for the second transducer unit; and
    cutting each of the transducer units into a plurality of transducer elements,
    further comprising attaching a matching layer to the piezoelectric layer before fabricating the plurality of conductive through vias, and where fabricating the plurality of conductive through vias comprises cutting the plurality of trenches entirely through both the matching layer and the piezoelectric layer prior to the filling of the plurality of trenches.

2. The method of claim 1, further comprising fabricating a plurality of non-conductive vias in the piezoelectric layer before cutting the piezoelectric layer into the plurality of transducer units by cutting a second plurality of trenches into, but not through, the piezoelectric layer and filling the second plurality of trenches with a dielectric material.

3. The method of claim 1, further comprising attaching a dematching layer to the piezoelectric layer before fabricating the plurality of conductive through vias, and where fabricating the plurality of conductive through vias comprises cutting the plurality of trenches through both the piezoelectric layer and the dematching layer.

4. The method of claim 3, further comprising fabricating a plurality of non-conductive vias by cutting a second plurality of trenches through the dematching layer and into, but not through, the piezoelectric layer after attaching the piezoelectric layer to the dematching layer, and filling the second plurality of trenches with a dielectric material.

5. The method of claim 1, further comprising attaching a dematching layer to the piezoelectric layer before fabricating the plurality of conductive through vias.

6. The method of claim 5, further comprising fabricating a plurality of non- conductive vias through the dematching layer and into, but not through, the piezoelectric layer after attaching the dematching layer and the matching layer to the piezoelectric layer.

7. The method of claim 1, wherein cutting each of the transducer units into the plurality of transducer elements comprises cutting each of the transducer units into a matrix array.

8. The method of claim 2, wherein cutting each of the transducer units into the plurality of transducer elements comprises cutting each of the transducer units into a linear array.

9. The method of claim 3, wherein cutting each of the transducer units into the plurality of transducer elements comprises cutting each of the transducer units into a matrix array.

10. The method of claim 4, wherein cutting each of the transducer units into the plurality of transducer elements comprises cutting each of the transducer units into a linear array.

11. The method of claim 5, wherein cutting each of the transducer units into the plurality of transducer elements comprises cutting each of the transducer units into a matrix array.

12. The method of claim 6, wherein cutting each of the transducer units into the plurality of transducer elements comprises cutting each of the transducer units into a linear array.

13. A method for making a plurality of ultrasound probes comprising:
    providing a piezoelectric layer having a first surface and a second surface, where the second surface is on an opposite side of the piezoelectric layer from the first surface;
    attaching a first conductive layer to the first surface of the piezoelectric layer;
    attaching a second conductive layer to the second surface of the piezoelectric layer;
    fabricating a plurality of conductive through vias extending from the first surface to the second surface of the piezoelectric layer, where fabricating the plurality of conductive through vias comprises cutting a plurality of trenches through the piezoelectric layer and entirely filling each of the plurality of trenches with an electrically conductive material;

cutting the piezoelectric layer into a plurality of transducer units after fabricating the plurality of conductive through vias, the plurality of transducer units comprising a first transducer unit and a second transducer unit, wherein said cutting the piezoelectric layer into the plurality of transducer units comprises cutting along one of the plurality of conductive through vias to separate the first transducer unit from the second transducer unit, wherein said cutting along the one of the plurality of conductive through vias leaves a first portion of the conductive material from the one of the plurality of conductive through vias on the first transducer unit and a second portion of the conductive material from the one of the plurality of conductive through vias on the second transducer unit, wherein the first portion of the conductive material provides a first electrical connection between the first conductive layer and the second conductive layer for the first transducer unit and the second portion of the conductive material provides a second electrical connection between the first conductive layer and the second conductive layer for the second transducer unit; and cutting each of the transducer units into a plurality of transducer elements; and securing each one of the plurality of transducer units into a different ultrasound probe body, further comprising attaching a matching layer to the piezoelectric layer before fabricating the plurality of conductive through vias, and where fabricating the plurality of conductive through vias comprises cutting the plurality of trenches entirely through both the matching layer and the piezoelectric layer prior to the filling of the plurality of trenches.

14. The method of claim 13, further comprising fabricating a plurality of non-conductive vias by cutting a second plurality of trenches into, but not through, the piezoelectric layer and filling the second plurality of trenches with a non-conductive material before cutting the piezoelectric layer into the plurality of transducer units.

15. The method of claim 13, further comprising attaching a dematching layer to the piezoelectric layer before fabricating the plurality of conductive through vias, and where fabricating the plurality of conductive through vias comprises cutting the plurality of trenches through both the piezoelectric layer and the dematching layer.

16. The method of claim 15, further comprising fabricating a plurality of non-conductive vias by cutting through the dematching layer and into to obtain the plurality of trenches, but not through, the piezoelectric layer after attaching the piezoelectric layer to the dematching layer and filling the plurality of trenches with a dielectric material.

17. The method of claim 13, further comprising attaching a dematching layer to the piezoelectric layer before fabricating the plurality of conductive through vias.

18. The method of claim 17, further comprising fabricating a plurality of non-conductive vias through the dematching layer and into, but not through, the piezoelectric layer after attaching the dematching layer and the matching layer to the piezoelectric layer.

19. The method of claim 1, wherein the matching layer has an acoustic impedance between an acoustic impedance of the piezoelectric layer and an acoustic impedance of tissue.

20. The method of claim 13, wherein the matching layer has an acoustic impedance between an acoustic impedance of the piezoelectric layer and an acoustic impedance of tissue.

* * * * *